United States Patent [19]

Raykovitz et al.

[11] Patent Number: 4,704,110

[45] Date of Patent: Nov. 3, 1987

[54] HOT MELT PRESSURE SENSITIVE POSITIONING ADHESIVES

[75] Inventors: Gary F. Raykovitz, Flemington; Catherine Salerno, Millington, both of N.J.

[73] Assignee: National Starch and Chemical Corporation, Bridgewater, N.J.

[21] Appl. No.: 877,031

[22] Filed: Jun. 20, 1986

[51] Int. Cl.$^4$ .............................................. A61F 13/16
[52] U.S. Cl. ..................................... 604/366; 604/389
[58] Field of Search ..................... 604/389, 385.1, 381, 604/378, 372, 371, 370, 367, 366, 365

[56] References Cited

U.S. PATENT DOCUMENTS 4,627,847  12/1986  Puletti et al. ........................ 604/366

OTHER PUBLICATIONS

Firestone Synthetic Rubber and Latex Co., Technical Service Report 6069, "Stereon® 840A for Hot Melt Adhesives Applications", Jan. 14, 1986.

Primary Examiner—John D. Yasko
Attorney, Agent, or Firm—Ellen T. Dec; Edwin M. Szala

[57] ABSTRACT

An absorbent article comprising an elongated absorbant pad having a body facing surface and a garment facing surface, a portion of the garment facing surface being coated with a hot melt pressure sensitive adhesive composition comprising a styrene-butadiene-styrene block or multi-block copolymer containing 35 to 55 parts styrene per 100 parts copolymer, a tackifying resin, a naphthenic or paraffinic oil, and an antioxidant.

15 Claims, No Drawings

HOT MELT PRESSURE SENSITIVE POSITIONING ADHESIVES

BACKGROUND OF THE INVENTION

A variety of absorbent structures, for example, sanitary napkins, panty liners and diaper liners for rubber pants, are constructed using pressure sensitive adhesives as positioning adhesives for attaching the article to the supporting garment.

There are a number of critical properties needed for these applications, specifically, the viscosity profile must be such that the adhesive will flow onto and partially penetrate the surface to which it is applied, yet allow a significant amount of the adhesive to remain on the exposed surface. Further, the adhesive coating must have good bond strength with high initial tack, yet the adhesive film must not transfer to the garment or cause pulling of the fibers or tearing of the garment when the absorbent article is removed.

Hot melt pressure sensitive adhesives are most commonly used for this positioning purpose with those disclosed in U.S. Pat. No. 4,136,699 being representative of the adhesives in current commercial use. In order to obtain the necessity properties, the compositions disclosed in U.S. Pat. No. 4,136,699 require the use of specific block copolymers wherein the mid-block is hydrogenated and wherein relatively large amounts of oil are needed in proportion to the amount of block copolymer. These hydrogenated copolymers are relatively expensive raw materials and are difficult to tackify.

It is an object of the present invention to prepare a hot melt pressure sensitive adhesive composition suitable for use as a positioning adhesive. More specifically, the adhesive compositions disclosed herein are prepared utilizing more economical, more easily tackifiable raw materials which unexpectedly produce stronger bonds than are found with the current commercial products with no adhesive transfer onto the undergarment.

SUMMARY OF THE INVENTION

A hot melt pressure sensitive adhesive suitable for use as a positioning adhesives is prepared comprising:

20 to 40% by weight of a styrene-butadiene-styrene block or multi-block copolymer containing 38 to 55 parts styrene per 100 parts copolymer;

30 to 70% by weight of a tackifying resin selected from the group consisting of modified hydrogenated rosins; glycerol and pentaerythritol esters of modified hydrogenated rosins; copolymers and terpolymers of natural terpenes; polyterpene resins having a softening point, as determined by ASTM method E28-58T, of from about 80 to 150° C.; aromatic petroleum hydrocarbon resins and the hydrogenated derivatives thereof; and copolymers of aliphatic and aromatic monomers;

10 to 30% by weight of naphthenic or paraffinic oil; and 0.1 to 2% by weight of an antioxidant;
wherein the ratio of oil to copolymer is 1:1 or less.

Thus the present invention is directed to absorbent articles comprising an elongated absorbent pad having a body facing surface and a garment facing surface, a portion of the garment facing surface being coated with the hot melt adhesive composition described above.

DETAILED DESCRIPTION OF THE PREFERRED EMBODIMENTS

The block copolymers used herein are recognized as linear A-B-A triblock copolymers or radial-block copolymers, or as A-B-A-B-A-B multi-block copolymers where the A block is styrene and the B block is butadiene and wherein the copolymer contains 38 to 55 parts styrene per 100 parts copolymer. These copolymers may be prepared using methods taught, for example, in U.S. Pat. Nos. 3,239,478; 3,427,269; 3,700,633; 3,753,936; and 3,932,327. Alternatively, they may be obtained from Firestone under the tradenames Stereon 840 A and Stereon 845, from Shell under the tradename DX1150 and from Enichem (Italy) under the tradename Sol T162.

The tackifying resins useful in these adhesive compositions can be hydrocarbon resins, synthetic polyterpenes, hydrogenated rosin esters, and the like. More particularly, the useful tackifying resins include any compatible resins or mixtures thereof such as (1) glycerol and pentaerythritol esters of modified hydrogenated rosins, such, for example as the glycerol ester of hydrogenated rosin, (2) copolymers and terpolymers of natural terpenes, e.g. styrene/terpene and alpha methyl styrene/terpene; (3) polyterpene resins having a softening point, as determined by ASTM method E28-58T, of from about 80 to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are (4) the hydrogenated polyterpene resins; and (5) copolymers of aliphatic and aromatic monomers such as Wingtack 86 available from Goodyear Tire and Rubber Company. While other known tackifying resins are not useful as the sole tackifier in the composition, it is possible to obtain satisfactory results utilizing a blend of tackifiers where a substantial portion of the blend is comprised of one of the tackifiers represented above.

The selection of the particular tackifying agent is, in large part, dependent upon the specific block copolymers employed. Generally the tackifier is present in the hot melt adhesive in an amount of 30–70%, preferably 50 to 60%, by weight.

Various plasticizing or extending oils are also present in the composition in amounts of 10% to about 30%, preferably 15 to 20%, by weight in order to provide wetting action and/or viscosity control It is desirable that the amount of oil present in the adhesive not exceed the amount of the block polymer. The usual plasticizing oils such as paraffinic and naphthenic oils are preferred; however, the invention also contemplates the use of the olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, or the like having average molecular weights between about 350 and about 10,000. Vegetable and animal oils include glyceryl esters of the usual fatty acids and polymerization products thereof. Additionally, some or all of the oil or some portion of the tackifying resin may be replaced by a liquid tackifying resins such as Wingtack 10 (a low molecular weight liquid aliphatic synethetic polyterpene plasticizing resin).

Various petroleum derived waxes may also be used in amounts less than about 15% by weight of the composition in order to impart fluidity in the molten condition of the adhesive and flexibility to the set adhesive, and to serve as a wetting agent. The term "petroleum derived wax" includes both paraffin and microcrystalline waxes having melting points within the range of 54-110° C. as well as synthetic waxes such as low molecular weight polyethylene or Fisher-Tropsch waxes.

Among the applicable stabilizers or antioxidants utilized herein are included high molecular weight hindered phenols and multifunctional phenols such as suflur and phosphorous-containing phenols. Hindered phenols are well known to those skilled in the art and may be characterized as phenolic compounds which also contain sterically bulky radicals in close proximity to the phenolic hydroxyl group hereof. In particular, tertiary butyl groups generally substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris (3,5-di-tert-butyl-4-hydroxybenzyl)benzene; pentaerythrityl tetrakis-3(3,5-di-tert-butyl-4-hydroxyphenyl)propionate; n-octadecyl-3(3,5-di-tert-butyl-4-hydroxyphenyl)-propionate; 4,4'methylenebis (2,6-tert-butylphenol); 4,4'-thiobis (6-tert-butyl-o-cresol); 2,6-ditertbutylphenol; 6-(4-hydroxyphenoxy)-2,4-bis-(n-octyl-thio)-1,3,5-triazine; di-n-octadecyl 3,5-di-tert-butyl-4-hydroxy-benzyl-phosphonate; 2-(n-octylthio)ethyl 3,5-di-tert-butyl--4-hydroxy-benzoate; and sorbitol hexa[3-(3-di-tert-butyl-4-hydroxyphenyl)-propionate]; zinc di-n-butyl dithiocarbamate and zinc diethyl dithiocarbamate.

The performance of these antioxidants may be further enhanced by utilizing, in conjunction therewith known synergists such, for example, as thiodipropionate esters and phosphites, particularly useful is distearylthiodipropionate.

These stabilizers are generally present in amounts of about 0.1 to 2 weight percent, preferably 0.25 to 1.0%.

In formulating the hot melt adhesives of the present invention, the styrene-butadiene copolymer is used in an amount of 20-40% by weight, preferably 25 to 35%; with 30-70%, preferably 50-60%, of a tackifier; 10-30%, preferably 15-20%, of a plasticizing oil and a small effective amount of an antioxidant. Other additives such as plasticizers, pigments, dystuffs conventionally added to hot melt adhesives for the various end uses contemplated may also be incorporated in minor amounts into the formulations of the present invention.

The adhesive compositions are prepared by blending the components in the melt at a temperature of about 130-200° C. until a homogeneous blend is obtained, approximately 2 hours. Various methods of blending are known to the art and any method that produces a homogeneous blend is satisfactory. An exemplary procedure involves placing the block copolymer, antioxidants and a portion of the oil in a jacketed mixing kettle, for example in a jacketed heavy duty mixer of the Baker-Perkins type, which is equipped with rotors and thereupon raising the temperature to a range of from about 120° to 180° C. When the mixture has been masticated to a uniform consistency, the tackifying resin and the remainder of the oil are gradually added in order to avoid the formation of lumps. Mixing and heating are continued until a smooth, homogeneous mass is obtained whereupon the remainder of the tackifying resin and the oil are thoroughly and uniformly admixed therewith. The resultant hot melt adhesives are generally produced in bulk form and packaged in release coated containers.

The resulting hot-melt pressure sensitive adhesive, once it is heated to a temperature where it will flow readily, can be applied directly to the outer covering layer of the absorbent structure or article or it may be reverse (transfer) coated onto release paper using any of the techniques known in the art, including flow coating, roller coating, knife coating, or the like. The adhesive can also be extruded into place by using a hot-melt extruder or die face.

In the following illustrative examples, all parts are by weight and all temperatures in degrees Celsius unless otherwise specified.

EXAMPLES

A series of adhesive formulations were prepared based on Stereon 845, a multi-block copolymer available from Shell containing approximately 50% styrene, varying the tackifying agent used.

| Ingredient | Formulation (weight %) | | | | | |
|---|---|---|---|---|---|---|
| | 1 | 2 | 3 | 4 | 5 | 6 |
| Stereon 845 | 27.5 | 27.5 | 27.5 | 27.5 | 27.5 | 27.5 |
| Naphthenic oil | 7.5 | 7.5 | 7.5 | 7.5 | 7.5 | 7.5 |
| Wingtack 10 (1) | 10 | 10 | 10 | 10 | 10 | 10 |
| Arkon M 100 (2) | 55 | — | — | — | — | — |
| Permalyn 85 (3) | — | 55 | — | — | — | — |
| Zonatac lite 105 (4) | — | — | 55 | — | — | — |
| Escorez 5300 (5) | — | — | — | 55 | — | — |
| Foral 105 (6) | — | — | — | — | 55 | — |
| Wingtack 86 (7) | — | — | — | — | — | 55 |
| Irganox 1010 (8) | 0.25 | 0.25 | 0.25 | 0.25 | 0.25 | 0.25 |
| Irgaphos 168 (8) | 0.25 | 0.25 | 0.25 | 0.25 | 0.25 | 0.25 |

(1) Wingtack 10 is a liquid tackifying resin available from Goodyear Tire and Rubber Company.
(2) Arkon M100 is a hydrogenated aromatic tackifying resin available from Arakawa K.K. (Japan).
(3) Permalyn 85 is a glycerol ester of resin available from Hercules Chemical.
(4) Zonatac lite 105 is a aromatic modified terpene resin available from Arizona Chemical.
(5) Escorez 5300 is a hydrogenated dicyclopentadiene resin available from Exxon Corpration.
(6) Foral 105 is a hydrogenated rosin ester available from Hercules Chemical.
(7) Wingtack 86 is an aliphatic-aromatic copolymer available from Goodyear Tire and Rubber Company.
(8) Antioxidant system.

Another series of adhesive formulations was prepared varying the block copolymers employed.

| Ingredient | % Styrene | Formulation (weight %) | | | |
|---|---|---|---|---|---|
| | | 7 | 8 | 9 | 10 |
| Wingtack 86 | — | 55 | 55 | 55 | 55 |
| Kraton 1102 (9) | 28% | 27.5 | — | — | — |
| Stereon 840A | 40% | — | 27.5 | — | — |
| DX 1150 (10) | 38% | — | — | 27.5 | — |
| Sol T162 (11) | 40% | — | — | — | 27.5 |
| Naphthenic Oil | — | 7.5 | 7.5 | 7.5 | 7.5 |
| Wingtack 10 | — | 10 | 10 | 10 | 10 |
| Irganox 1010 | — | 0.25 | 0.25 | 0.25 | 0.25 |
| Irgaphos 168 | — | 0.25 | 0.25 | 0.25 | 0.25 |

(9) A block copolymer available from Shell Chemical containing 28% styrene.

-continued

(10) A block polymer available from Shell Chemical containing 38% styrene.
(11) A block copolymer available from Enichem (Italy).

As a comparison, a formulation was prepared from 15.75 parts Kraton G1650 (styrene=28–30%), 25 parts oil, 59-25 parts Wingtack 95 and an antioxidant according to the teachings of U.S. Pat. No. 4,136,699.

Test procedures utilized herein are as follows:

Samples were prepared for testing by coating a 1.75–2.25 mil thickness of the adhesive on a Mylar substrate (trademark of Dow Chemical Corp.). After conditioning overnight, 1 inch by 3 inch (2.54 by 7.82 cm.) strips were cut in the X- machine direction. All tests were performed on samples as initially prepared and then repeated after subjecting the adhesives to heat aging at 175° C. for 24 hours.

Dynamic Cotton Shear:

The coated samples were laminated to cotton knit fabric (placed on glass) using two passes with a 4.5 lb. (2 kg) roller. Immediately after lamination, the coated sample was pulled from the cotton knit using the shear mode on an Instron Tester at a crosshead speed of 20 inches (50 cm) per minute. Values shown are for an average of at least three samples and are expressed in grams per linear inch.

180° Cotton Peel:

The coated samples was laminated to cotton knit fabric by placing the knit on glass plates in an oven equilibrated to 40° C. and placing the sample on top of the knit with a load of 150 grams per square inch for a period of 60 minutes. The sample was then peeled away from the cotton knit in a 180° direction using an Instron Tester at crosshead speed of 20 inches (50 cm) per minute. Values shown are for an average of at least three samples and are expressed in grams per linear inch.

Cotton Peel Retention:

The coated sample was laminated to cotton knit as for the Dynamic Shear Test. Then using a crosshead speed of 20 inches (50 cm) per minute, the coated samples were pulled away from the cotton knit immediately and after 30 minutes conditioning at room temperature. Values are shown in grams per linear inch for an average of at least three samples at each time interval.

Transfer:

The coated sample was laminated to cotton knit fabric by placing the knit on glass plates in an oven equilibrated to 49° C. and laminating with a 800 gram per square inch load for 24 hours. The sample was then peeled away from the cotton knit in 180° direction on an Instron Tester at crosshead speed of 20 inches (50 cm) per minute. Values shown are for an average of at least three samples and are expressed in grams per linear inch. The adhesive residue left on the cotton knit is noted qualitatively.

Heat Stability:

Two hundred grams of the adhesive were placed in a clean glass jar, tightly covered with aluminum foil and placed in an oven equilibrated to 176° for 24 hours. The adhesive was then examined visually for stains, char, separation, gel, edge rim and color. The viscosity was measured and compared with the initial viscosity.

Test results for formulations 1–10 as well as the control are presented in Table I.

TABLE I

| Test Formulation | 1 | 2 | 3 | 4 | 5 | 6 | 7 | 8 | 9 | 10 | Control |
|---|---|---|---|---|---|---|---|---|---|---|---|
| Cotton Peel (initial) | 170 | 468 | 213 | 43 | 240 | 255 | 400 | 317 | 125 | 132 | 225 |
| (after aging) | 155 | 600 | 218 | 45 | 295 | 268 | 415 | 270 | 107 | 125 | 257 |
| Peel Retention (initial) | 297 | 699 | 245 | 8 | 666 | 932 | 1035 | 1041 | 518 | 890 | 932 |
| (after aging) | 327 | 611 | 218 | 21 | 690 | 950 | 1078 | 1171 | 690 | 775 | 869 |
| Peel Retention* (initial) | 294 | 630 | 224 | 14 | 763 | 893 | 920 | 950 | 521 | 751 | 893 |
| (after aging) | 288 | 593 | 248 | 29 | 702 | 787 | 781 | 1111 | 490 | 572 | 412 |
| Dynamic Cotton Shear (initial) | 1233 | 2783 | 1000 | 83 | 2417 | 3567 | 4367 | 4083 | 2550 | 3567 | 3567 |
| (after aging) | 1100 | 2850 | 1233 | 67 | 1867 | 3367 | 4450 | 4050 | 3500 | 2967 | 3133 |
| Transfer (initial) | 1060 | 2467 | 2133 | 483 | 2125 | 1275 | 2583 | 2225 | 4313 | 867 | 1275 |
| (after aging) | 1067 | 2517 | 1342 | 433 | 1700 | 1050 | 2900 | 2217 | 1083 | 617 | 983 |
| Qualitative Transfer (initial) | none | moderate | none | none | none | none | heavy | none | none | none | none |
| (after aging) | none | moderate | none | none | none | none | heavy | none | none | none | none |
| Heat Stability | good | good | good | good | good | good | good | good | good | good | good |

*Test procedure repeated after conditioning at room temperature for 1/2 hour.

The results presented above show that only when adhesives are formulated using the high styrene content block copolyer with the specific classes of tackifying agents described herein are compositions obtained characterized by a high degree of adhesion and low transfer as desired for commercial positioning adhesive applications. Thus, formulations 1, 3, 5, 6, 8, 9 and 10 prepared with block copolymers containing at least 38% styrene and with tackifiers from the specified classes provided adhesive compositions which would be satisfactory for commercial application and in some cases, gave adhesive strength values greater than or equivalent to those achieved with the present commercially utilized product with little or no increase in transfer. In contrast, use of the high styrene polymers with other tackifiers in formulations 2, 4, and 7 exhibited substantially poorer adhesive strength values or undesirable transfer.

I claim:

1. An absorbent article comprising an elongated absorbent pad having a body facing surface and a garment facing surface, a portion of the garment facing surface being coated with a hot melt pressure sensitive adhesive composition comprising:
   20 to 40% by weight of a styrene-butadiene-styrene block or multi-block copolymer containing 38 to 55 parts styrene per 100 parts copolymer;
   30 to 70% by weight of a tackifying resin selected from the group consisting of modified hydrogenated rosins; glycerol and pentaerythritol esters of modified hydrogenated rosins; copolymers and terpolymers of natural terpenes; polyterpene resins having a softening point, as determined by ASTM method E28-58T, of from about 80 to 150° C.;

aromatic petroleum hydrocarbon resins and the hydrogenated derivatives thereof; and copolymers of aliphatic and aromatic monomers;

10 to 30% by weight of a naphthenic or paraffinic oil; and 0.1 to 2% by weight of an antioxidant;

wherein the ratio of oil to copolymer is 1:1 or less.

2. The article of claim 1 wherein the adhesive contains an A-B-A-B-A-B type copolymer.

3. The article of claim 1 wherein the adhesive contains a multi-block copolymer containing 45-55% styrene.

4. The article of claim 1 wherein the adhesive contains as a tackifying resin a copolymer of aliphatic and aromatic monomers.

5. The article of claim 1 wherein the adhesive comprises 25-35% of the block polymer, 50-60% of the tackifying resin and 15-20% of the oil.

6. The article of claim 1 wherein the adhesive composition additionally contains up to 15% by weight of a wax.

7. The article of claim 1 wherein some or all of the oil or some of the tackifying resin in the adhesive composition is replaced by a liquid aliphatic plasticizing resin.

8. The article of claim 7 wherein the liquid plasticizing resin is a synthetic polyterpene resin.

9. The article of claim 1 comprising a sanitary napkin.

10. The article of claim 1 comprising a panty liner.

11. The article of claim 1 comprising a diaper insert.

12. An absorbent article comprising an elongated absorbent pad having a body facing surface and a garment facing surface, a portion of the garment facing surface being coated with a hot melt pressure sensitive adhesive composition comprising:

25 to 35% by weight of a styrene-butadiene-styrene multi-block copolymer containing 45 to 55 parts styrene per 100 parts copolymer;

50 to 60% by weight of a copolymer of aliphatic and aromatic monomers;

15 to 20% by weight of a naphthenic or paraffinic oil; and 0.1 to 2% by weight of an antioxidant.

13. The article of claim 12 wherein some or all of the oil or some of the tackifying resin in the adhesive composition is replaced by a liquid aliphatic plasticizing resin.

14. The article of claim 13 wherein the liquid plasticizing resin is a synthetic polyterpene resin.

15. The article of claim 12 comprising a sanitary napkin.

* * * * *